US006640120B1

(12) United States Patent
Swanson et al.

(10) Patent No.: US 6,640,120 B1
(45) Date of Patent: Oct. 28, 2003

(54) PROBE ASSEMBLY FOR MAPPING AND ABLATING PULMONARY VEIN TISSUE AND METHOD OF USING SAME

(75) Inventors: David K. Swanson, Campbell, CA (US); Anant V. Hegde, Newark, CA (US); Anna Hartzog, Sunnyvale, CA (US); Alan McMillan, Westchester, PA (US); Dennis O'Brien, Santa Barbara, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 161 days.

(21) Appl. No.: 09/684,559

(22) Filed: Oct. 5, 2000

(51) Int. Cl.[7] .............................................. A61B 18/18
(52) U.S. Cl. .......................... 600/374; 606/41; 607/101
(58) Field of Search ................................. 607/101–102, 607/122; 606/111, 46, 47–52; 600/374

(56) References Cited

U.S. PATENT DOCUMENTS

| | | | |
|---|---|---|---|
| 5,255,678 A | * 10/1993 | Deslauries et al. | 607/122 |
| 5,263,493 A | 11/1993 | Avitall | |
| 5,324,284 A | 6/1994 | Imran | |
| 5,411,025 A | 5/1995 | Webster, Jr. | |
| 5,425,703 A | 6/1995 | Feiring | |
| 5,465,717 A | 11/1995 | Imram et al. | |
| 5,471,982 A | 12/1995 | Edwards et al. | |
| 5,575,810 A | 11/1996 | Swanson et al. | |
| 5,595,183 A | 1/1997 | Swanson et al. | |
| 5,628,313 A | 5/1997 | Webster, Jr. | |
| 5,722,403 A | 3/1998 | McGee et al. | |
| 5,797,903 A | 8/1998 | Swanson et al. | |
| 5,925,038 A | * 7/1999 | Panescu et al. | 606/41 |
| 6,009,877 A | * 1/2000 | Edwards | 606/41 |
| 6,012,457 A | 1/2000 | Lesh | |
| 6,014,579 A | * 1/2000 | Pomeranz et al. | 600/374 |
| 6,036,689 A | * 3/2000 | Tu et al. | 606/41 |
| 6,119,030 A | 9/2000 | Morency | |
| 6,405,732 B1 | * 6/2002 | Edwards et al. | 606/41 |

FOREIGN PATENT DOCUMENTS

WO  WO 00/56237  9/2000

* cited by examiner

Primary Examiner—Linda C. M. Dvorak
Assistant Examiner—David M Ruddy
(74) Attorney, Agent, or Firm—Bingham McCutchen LLP

(57) ABSTRACT

The present invention relates to a probe assembly for mapping and ablating pulmonary vein tissue and method of using the same. The probe assembly includes an expandable and collapsible basket assembly having multiple splines. One or more of the splines carry one or more electrodes adapted to sense electrical activity in the pulmonary vein tissue. The basket assembly defines an interior, and a microporous expandable and collapsible body is disposed in the interior of the basket assembly and defines an interior adapted to receive a medium containing ions. An internal electrode is disposed within the interior of the body and is adapted to transmit electrical energy to the medium containing ions. The body includes at least one microporous region having a plurality of micropores therein sized to pass ions contained in the medium without substantial medium perfusion therethrough, enabling ionic transport of electrical energy from the internal electrode, through ion-containing medium to an exterior of the body to ablate pulmonary vein tissue. In other aspects of the invention, the microporous body may be replaced by a non-porous expandable and collapsible body that receives a fluid medium for expanding the non-porous body to exclude blood from the electrodes on the splines, or the probe assembly may not include any expandable and collapsible body in the basket assembly interior (one or more electrodes on splines sense electrical activity in the pulmonary vein tissue and ablate the pulmonary vein tissue).

17 Claims, 12 Drawing Sheets

PROBE ASSEMBLY FOR MAPPING AND ABLATING PULMONARY VEIN TISSUE AND METHOD OF USING SAME

FIELD OF THE INVENTION

The present invention relates, in general, to electrode probe assemblies and methods for mapping and/or ablating body tissue, and, in particular, to electrode probe assemblies and methods for mapping and/or ablating pulmonary vein tissue.

BACKGROUND OF THE INVENTION

Aberrant conductive pathways can develop in heart tissue and the surrounding tissue, disrupting the normal path of the heart's electrical impulses. For example, anatomical obstacles, called "conduction blocks," can cause the electrical impulse to degenerate into several circular wavelets that circulate about the obstacles. These wavelets disrupt the normal activation of the atria or ventricles. The aberrant conductive pathways create abnormal, irregular, and sometimes life-threatening heart rhythms called arrhythmias. An arrhythmia can take place in the atria, for example, as in atrial tachycardia ("AT") or atrial fibrillation ("AF"). The arrhythmia can also take place in the ventricle, for example, as in ventricular tachycardia ("VT").

In treating arrhythmias, it is sometimes essential that the location of the sources of the aberrant pathways (called focal arrhythmia substrates) be located. Once located, the focal arrhythmia substrate can be destroyed, or ablated, e.g., by surgical cutting or the application of heat. In particular, ablation can remove the aberrant conductive pathway, thereby restoring normal myocardial contraction. An example of such an ablation procedure is described in U.S. Pat. No. 5,471,982 issued to Edwards et al.

Alternatively, arrhythmias may be treated by actively interrupting all of the potential pathways for atrial reentry circuits by creating complex lesion patterns on the myocardial tissue. An example of such a procedure is described in U.S. Pat. No. 5,575,810, issued Swanson et al.

Frequently, an arrhythmia aberration resides at the base, or within one or more pulmonary veins, wherein the atrial tissue extends. To treat such an aberration, physicians use multiple catheters to gain access into interior regions of the pulmonary vein tissue for mapping and ablating targeted tissue areas. A physician must carefully and precisely control the ablation procedure, especially during procedures that map and ablate tissue within the pulmonary vein. During such a procedure, the physician may introduce a mapping catheter to map the aberrant conductive pathway within the pulmonary vein. The physician introduces the mapping catheter through a main vein, typically the femoral vein, and into the interior region of the pulmonary vein that is to be treated.

Placement of the mapping catheter within the vasculature of the patient is typically facilitated with the aid of an introducer guide sheath or guide wire. The introducer guide sheath is introduced into the left atrium of the heart using a conventional retrograde approach, i.e., through the respective aortic and mitral valves of the heart. Alternatively, the introducer guide sheath may be introduced into the left atrium using a transeptal approach, i.e., through the atrial septum. In either method, the catheter is introduced through the introducer guide sheath until a probe assembly at a distal portion of the catheter resides within the left atrium. A detailed description of methods for introducing a catheter into the left atrium via a transeptal approach is disclosed in U.S. Pat. No. 5,575,810, issued to Swanson et al., which is fully and expressly incorporated herein by reference. Once inside the left atrium, the physician may deliver the probe assembly into a desired pulmonary vein by employing a steering mechanism on the catheter handle. The physician situates the probe assembly within a selected tissue region in the interior of the pulmonary vein, adjacent to the opening into the left atrium, and maps electrical activity in the pulmonary vein tissue using one or more electrodes of the probe assembly.

After mapping, the physician introduces a second catheter to ablate the aberrant pulmonary vein tissue. The physician further manipulates a steering mechanism to place an ablation electrode carried on the distal tip of the ablation catheter within the selected tissue region in the interior of the pulmonary vein. The ablation electrode is placed in direct contact with the tissue that is to be ablated. The physician directs radio frequency energy from the ablation electrode through tissue to an electrode to ablate the tissue and form a lesion.

Problems with this approach include the possibility of misdirecting or misplacing the ablation electrode and inadvertently ablating non-aberrant, i.e., healthy, pulmonary vein tissue. Further, this approach is time-consuming because the physician has to introduce and remove two catheters. This leads to more patient discomfort and room for physician error. Poorly controlled ablation in the pulmonary vein can result in pulmonary vein stenosis. The pulmonary vein stenosis can lead to pulmonary hypertension, pulmonary edema, necrosis of lung tissue, and even complete pulmonary failure of a lung or lung lobe. In severe and rare cases, the only treatment may be a lung transplant.

SUMMARY OF THE INVENTION

The present invention includes the following three main aspects that solve the problems with separate mapping catheters and ablation catheters for mapping electrical activity in pulmonary vein tissue and ablating the pulmonary vein tissue: 1) a probe assembly with a microporous ablation body used with a basket assembly for mapping and ablating pulmonary vein tissue; 2) a probe assembly with a basket assembly for mapping and ablating pulmonary vein tissue; and 3) a probe assembly with an expandable body used with a basket assembly for mapping and ablating pulmonary vein tissue. Each of these aspects is summarized in turn below.

1. Probe Assembly with an Expandable Body used with a Basket Assembly for Mapping and Ablating Pulmonary Vein Tissue A first aspect of the invention includes a probe assembly for mapping and ablating pulmonary vein tissue. The probe assembly includes an expandable and collapsible basket assembly including multiple splines, one or more of the splines carrying one or more electrodes adapted to sense electrical activity in the pulmonary vein tissue, the basket assembly defining an interior, a microporous expandable and collapsible body disposed in the interior of the basket assembly and defining an interior adapted to receive a medium containing ions, an internal electrode disposed within the interior of the body and adapted to transmit electrical energy to the medium containing ions, the body including at least one microporous region having a plurality of micropores therein sized to pass ions contained in the medium without substantial medium perfusion therethrough, to thereby enable ionic transport of electrical energy from the internal electrode, through the ion-containing medium to an exterior of the body to ablate pulmonary vein tissue. In an exemplary implementation of the first aspect, the microporous expandable and collapsible body is adapted to be maintained in an expanded condition at a substantially constant pressure by a continuous flow of the medium through the body, providing a cooling effect in the microporous body and the pulmonary vein tissue.

2. Probe Assembly with a Basket Assembly for Mapping and Ablating Pulmonary Vein Tissue A second aspect of the invention involves a probe assembly for mapping and ablating pulmonary vein tissue. The probe assembly includes an expandable and collapsible basket assembly including multiple splines, one or more of the splines carrying one or more electrodes, and at least one of the one or more electrodes adapted to sense electrical activity in the pulmonary vein tissue and ablate the pulmonary vein tissue.

3. Probe Assembly with an Expandable Body used with a Basket Assembly for Mapping and Ablating Pulmonary Vein Tissue A third aspect of the invention includes a probe assembly for mapping and ablating pulmonary vein tissue. The probe assembly includes an expandable and collapsible basket assembly including multiple splines, one or more of the splines carrying one or more electrodes adapted to sense electrical activity in the pulmonary vein tissue, the basket assembly defining an interior, and a non-porous expandable and collapsible body disposed in the interior of the basket assembly and defining an interior adapted to receive a fluid medium for expanding the expandable and collapsible body to exclude blood from the electrodes. In an exemplary implementation of the third aspect, the non-porous expandable and collapsible body is adapted to be maintained in an expanded condition at a substantially constant pressure by a continuous flow of the medium through the body, providing a cooling effect in the body and the pulmonary vein tissue.

Other and further objects, features, aspects, and advantages of the present inventions will become better understood with the following detailed description of the accompanying drawings.

BRIEF DESCRIPTION OF DRAWINGS

The drawings illustrate both the design and utility of preferred embodiments of the present invention, in which like elements are referred to with common reference numerals.

DETAILED DESCRIPTION OF THE PREFERRED EMBODIMENTS

The present invention involves a mapping and ablation probe assembly for a catheter that solves the problems described above associated with a separate mapping catheter for mapping electrical activity in pulmonary vein tissue and ablation catheter for ablating the pulmonary vein tissue. Three main aspects of the probe assembly are described below. The first aspect is a probe assembly with a microporous ablation body used with a basket assembly for mapping and ablating pulmonary vein tissue. Along with a description of this aspect of the probe assembly, an exemplary catheter system that is applicable to all three main aspects will also be described. The second aspect is a probe assembly with a basket assembly for mapping and ablating pulmonary vein tissue. The third aspect is a probe assembly with an expandable body used with a basket assembly for mapping and ablating pulmonary vein tissue. Each of these aspects will now be described in turn.

1. Probe Assembly with an Expandable Body used with a Basket Assembly for Mapping and Ablating Pulmonary Vein Tissue With reference to FIGS. 1 and 2, a catheter 10 including a probe assembly 14 for mapping and ablating pulmonary vein tissue and constructed in accordance with a first aspect of the invention will now be described. Although the probe assembly 14 and alternative probe assembly embodiments described further below are described in conjunction with mapping and ablating pulmonary vein tissue, it will be readily apparent to those skilled in the art that the probe assemblies may be used to map and ablate other body tissues such as, but not by way of limitation, myocardial tissue. Further, it should be noted, the probe assembly 14 and catheter 10 illustrated in drawings are not necessarily drawn to scale. The probe assembly 14 will first be described, followed by a description of the rest of the catheter system and a method of using the probe assembly.

Figure 2:
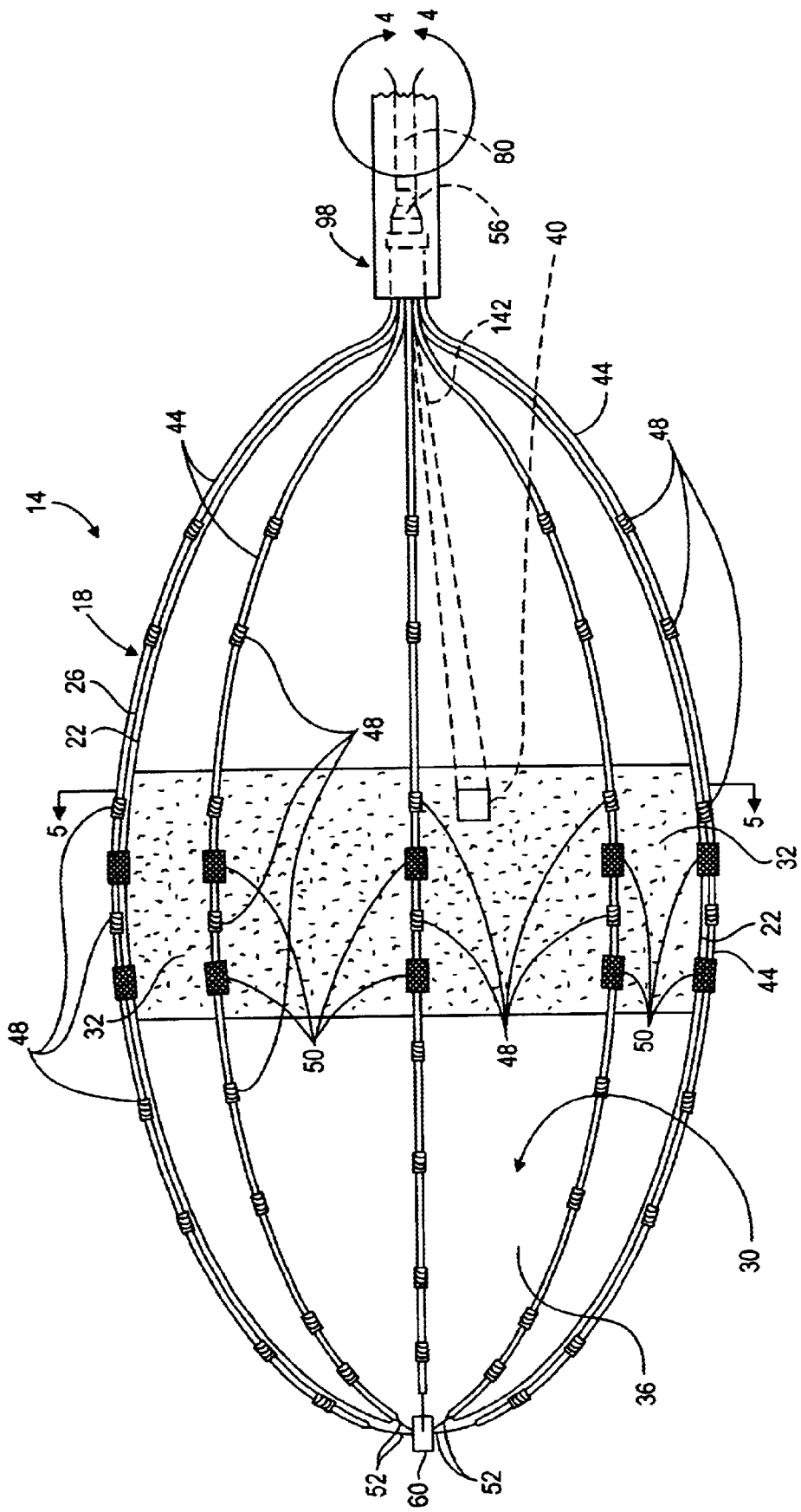
FIG. 2 is an enlarged elevational view of the probe assembly illustrated in FIG. 1, taken in the region of 2—2 of FIG. 1.

A. Probe Assembly:

With reference to FIG. 2, the probe assembly 14 may include an expandable and collapsible basket 18 and a microporous body 22 located in an interior region 26 of the basket 18.

The geometry of the microporous body 22 may be altered between a collapsed geometry (FIG. 6) and enlarged expanded geometry (FIGS. 2, 5) by injecting and removing a pressurized and conductive inflation medium 30 into and from an interior 36 of the microporous body 22. The pressurized inflation medium 30 also maintains the microporous body 22 in the expanded geometry. The inflation medium 30 is composed of an electrically conductive liquid that establishes an electrically conductive path from a ring electrode 40 to the surface of the microporous body 22. Preferably, the electrically conductive medium 30 possesses a low resistivity to decrease ohmic losses and, thus, ohmic heating effects, within the microporous body 22. The composition of the electrically conductive medium 30 can vary. In the illustrated embodiment, the electrically conductive medium 30 comprises a hypertonic saline solution having a sodium chloride concentration at or about 10% weight by volume. The medium may include a 70:30 mixture of 10% saline and radio-opaque solution. An exemplary radio-opaque solution that may be used is sold as Omnipaque® by Nycomed Amersham Imaging of Princeton, N.J. A medium 30 with a radio-opaque solution allows the body 22 to be visualized using fluoroscopy.

The ring electrode 40 is located within the interior region 36 of the microporous body 22. The ring electrode 40 transmits RF energy that is delivered to pulmonary vein tissue via ionic transport through the conductive inflation medium 30 and micropores in the microporous body 22. In this regard, the ring electrode 40 is composed of a material having both a relatively high electrical conductivity and a relatively high thermal conductivity, e.g., gold, platinum, or platinum/iridium.

It should be noted that the ring-like structure of the electrode 40 provides a relatively large circumferential exterior surface in communication with the inflation medium 30 in the interior region 36 of the microporous body 22, providing an efficient means of energizing the inflation medium 30. Although the electrode 40 is described as a ring, the electrode 40 can take the form of any suitable structure that can contact the inflation medium 30. The length of the electrode 40 can be accordingly varied to increase or decrease the amount of RF energy delivered to the inflation medium 30. The location of the electrode 40 can also be varied.

Although in the embodiment shown and described, the operative ablative element is a RF electrode 40 and tissue is ablated through the delivery of RF energy, in alternative embodiments, the ablative element may be adapted to ablate body tissue using an ultrasound transmitter, a laser, a cryogenic mechanism, or other similar means. For example, the body 22 may be adapted to receive a cryogenic medium to thereby enable cryogenic ablation of pulmonary vein tissue via said cryogenic medium and said body 22.

The microporous body 22 is preferably made of an electrically non-conductive material including micropores in at least a portion of the body 22. The micropores are preferably 0.0001 to about 0.1 microns in diameter. The microporous structure of the microporous body 22 acts as the energy-emitting surface, establishing ionic transport of RF energy from the RF electrode 40, through the inflation medium 30, and into the tissue outside of the microporous body 22, thereby creating a lesion.

The geometry of the energy-emitting surface of the microporous body 22 can be customized to more efficiently produce the desired lesion characteristics. In particular, the delivery of RF energy from the electrode 40 to the microporous body 22 can be concentrated in certain regions of the microporous body 22. For example, the microporous body 22 may include a microporous region 32 that runs around a central circumferential portion of the microporous body 22. Additionally or alternatively, the microporous region 32 may run along another portion of the body 22 such as adjacent to a proximal base of the body 22 or adjacent to a distal tip of the body 22. One way to concentrate the delivery of RF energy from one or more regions of the microporous body 22 is by masking the micropores of the microporous body 22 in the regions where RF energy delivery is not desired.

The electrical resistivity of the microporous body 22 has a significant influence on the tissue lesion geometry and controllability. Ablation with a low-resistivity microporous body 22 enables more RF power to be transmitted to the tissue and results in deeper lesions. On the other hand, ablation with a high-resistivity microporous body 22 generates more uniform heating, therefore improving the controllability of the lesion. Generally speaking, lower resistivity values for the microporous body 22 (below about 500 ohm-cm) result in deeper lesion geometries, while higher resistivity values for the microporous body 22 (above about 500 ohm-cm) result in shallower lesion geometries.

The electrical resistivity of the microporous body 22 can be controlled by specifying the pore size of the material, the porosity of the material (space on the body that does not contain material), and the water absorption characteristics (hydrophilic versus hydrophobic) of the material. In general, the greater the pore size and porosity, the lower the resistivity of the microporous body 22. In contrast, the lesser the pore size and porosity, the greater the resistivity of the microporous body 22. The size of the pores is selected such that little or no liquid perfusion through the pores results, assuming a maximum liquid pressure within the interior region of the microporous body 22. Thus, the pores are sized to pass ions contained in the medium without substantial medium perfusion therethrough to thereby enable ionic transport of electrical energy from the ion-containing medium 30 to an exterior of the body 22 to ablate pulmonary vein tissue.

In general, hydrophilic materials possess a greater capacity to provide ionic transfer of radio frequency energy without significant perfusion of liquid through the microporous body 22 than do hydrophobic materials. Additionally, hydrophilic materials generally have lower coefficients of friction with body tissues than have hydrophobic materials, facilitating routing of the catheter through the vasculature of the patient. Exemplary materials that can be used to make the microporous body 22 include, but not by way of limitation, regenerated cellulose, nylon, nylon 6, nylon 6/6, polycarbonate, polyethersulfone, modified acrylic polymers, cellulose acetate, poly(vinylidene fluoride), poly (vinylpyrrolidone), and a poly(vinylidene fluoride) and poly (vinylpyrrolidone) combination. A microporous body made of a poly(vinylidene fluoride) and poly(vinylpyrrolidone) combination is disclosed in Hegde, et al., U.S. Application No. (Unknown) entitled "POROUS MEMBRANES", filed on May 22, 2000, the specification of which is fully and expressly incorporated herein by reference. Also, further details concerning the manufacture of the microporous body 22, including the specification of the material, pore size, porosity, and water absorption characteristics of the material, are disclosed in Swanson, et al., U.S. Pat. No. 5,797,903, the specification of which is fully and expressly incorporated herein by reference.

The basket 18 includes multiple flexible splines 44. Each of the splines 44 is preferably made of a resilient inert material such as Nitinol metal or silicone rubber; however, other materials may be used. Multiple electrodes 48 are located on each spline 44. Connected to each mapping electrode 48 are signal wires 52 made from a highly conductive metal such as copper. The signal wires 52 preferably extend through each spline 44 and into catheter body 80. The splines 44 are connected to a base member 56 and an end member 60. The splines 44 extend circumferentially between the base member 56 and the end member 60 when in the expanded geometry. Plastic tubing may be used to cover the splines 44 and contain the signal wires 52 running from the electrodes 48.

Although the electrodes 48 are described below as mapping electrodes, in alternative embodiments, the electrodes 48 may be multi-functional electrodes used for mapping, pacing, and/or ablating body tissue. In a further embodiment, the splines 44 may not include any electrodes. Any or all of the embodiments described below may also include splines 44 having multi-functional electrodes 48 or no electrodes.

The basket 18 is shown with specific number of splines 44 and electrodes 48 for each spline 44, i.e., 8; however, it will be readily apparent to those skilled in the art that the number of splines 44 and/or the number of electrodes 48 per spline 44 may vary. For example, FIG. 3A depicts a basket structure with six splines 44 (two splines 44 are hidden from view), with some of the splines 44 having nine electrodes 48 and other splines 44 having ten electrodes 48. Further, the shape of the splines 44 and electrodes 48 may vary.

Because the electrodes 48 in this embodiment are mounted on flexible splines 44, when the basket 18 is expanded in the vasculature of a patient, the splines 44 conform to a large range of different vein sizes and shapes. The flexibility and resiliency of the splines 44 also allows for the basket structure to push outward on the tissue. This increases the friction between the electrodes 48 and the vein and thereby anchors the probe assembly 14 in position, yielding a more precise ablation location.

The splines 44 may carry one or more temperature sensors 50 that may take the form of thermistors, thermocouples, or the equivalent, and are in thermal conductive contact with the exterior of the probe assembly 14 to sense conditions in tissue outside the probe assembly 14 during ablation. The temperature sensors 50 may be located on the splines 44 such that when the splines 44 are expanded, the temperature sensors 50 are located at or near the largest diameter of the probe assembly 14. Although the basket 18 in FIG. 2 is shown with two temperature sensors 50 for each spline 44, it will be readily apparent to those skilled in the art that the number of temperature sensors 50 per spline 44 may vary.

Figure 3B:
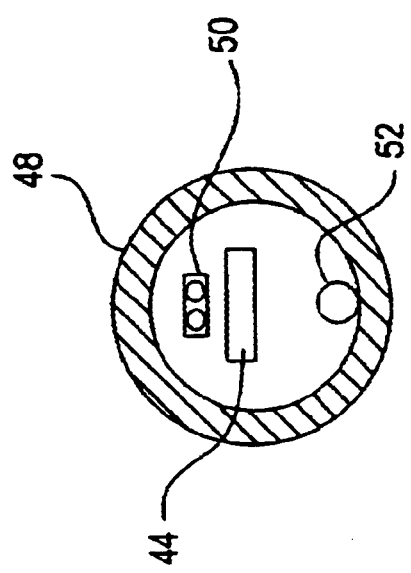
FIG. 3B is an enlarged cross sectional view of one of the splines of FIG. 3A taken along line 3B—3B.
Figure 3A:
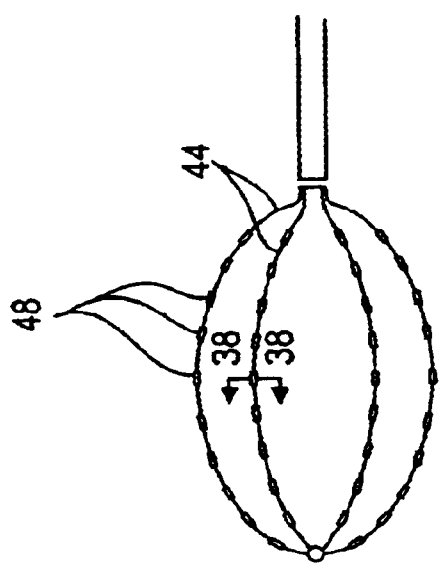
FIG. 3A is an enlarged side view of an alternative embodiment of a probe assembly with a fewer number of splines than that depicted in FIGS. 1 and 3.
Figure 4:
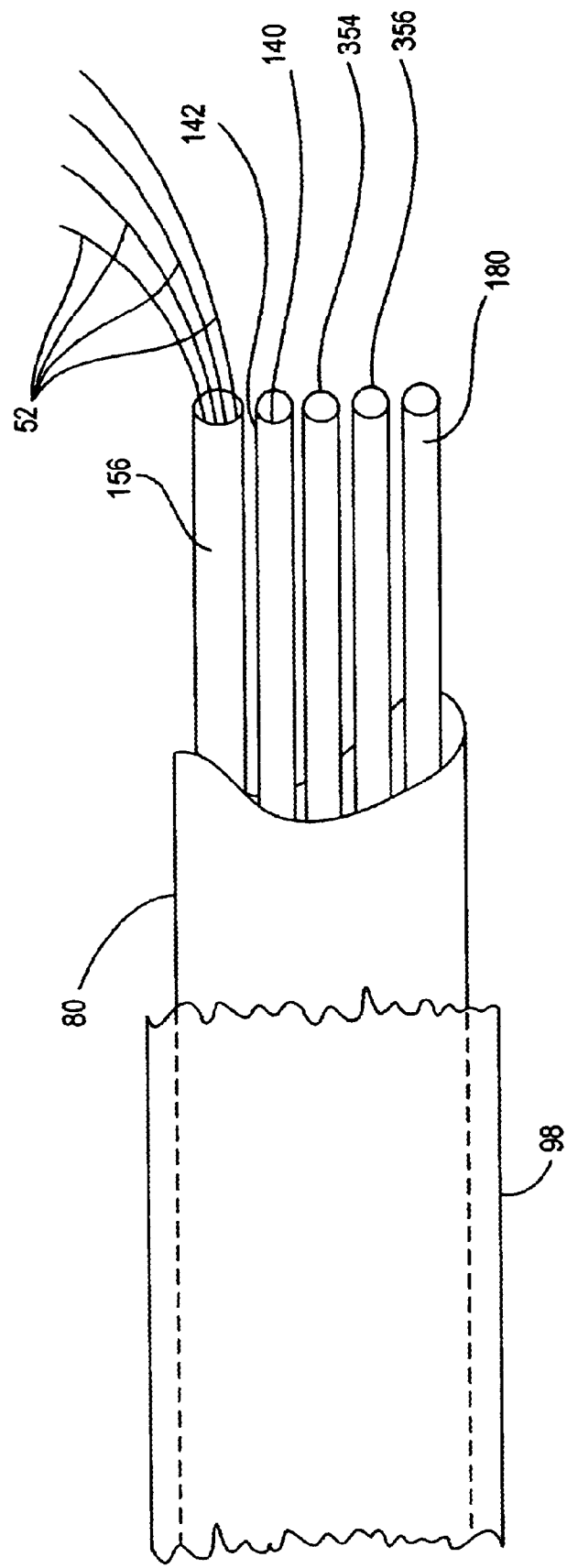
FIG. 4 is an enlarged side elevational view of a portion of the catheter, taken in the region of 4—4 of FIG. 2.

With reference to FIGS. 3A and 3B, in an alternative embodiment, the electrodes 48 may comprise rings that surround the temperature sensors 50, splines 44, and signal wires 52.

Figure 5:
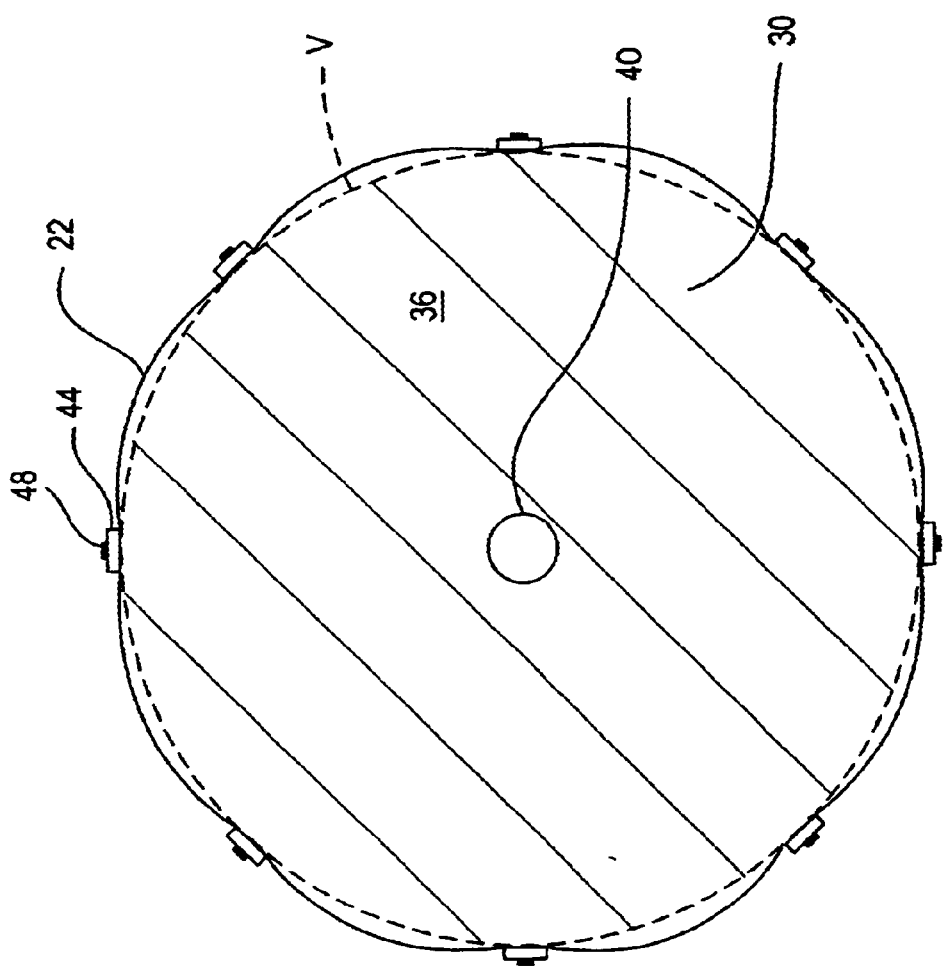
FIG. 5 is an enlarged cross sectional view of the probe assembly, taken along line 5—5 of FIG. 2.

With reference to FIG. 5, the microporous body 22 may include a construction that, when inflated, has a larger volume than the volume V defined by the expanded basket 18, causing the body 22 to extend or bulge between and beyond the circumferential region or volume V defined by the basket assembly 18 when the basket assembly 18 and the body 22 are in an expanded state. This may help put the microporous body 22 in more direct contact with the targeted pulmonary vein tissue, improving ablation treatment of the tissue. This may also cause the delivery of RF energy from the microporous body 22 to be concentrated in the bulging regions of the microporous body 22, which may be desirable depending on the targeted tissue that needs ablating. Additionally, the microporous body 22 restricts blood flow to the ablation area, which reduces the possibility of coagulated blood embolus. Finally, restricting blood flow renders the relationship between ablation parameters (power, time, and temperature) and lesion characteristics more predictable, since the important lesion parameters of energy loss attributable to the convective losses and to energy delivery are more predictable.

B. Catheter System.

With reference generally to FIGS. 1–4 and 6, the remaining components of the catheter system will now be described.

Figure 6:
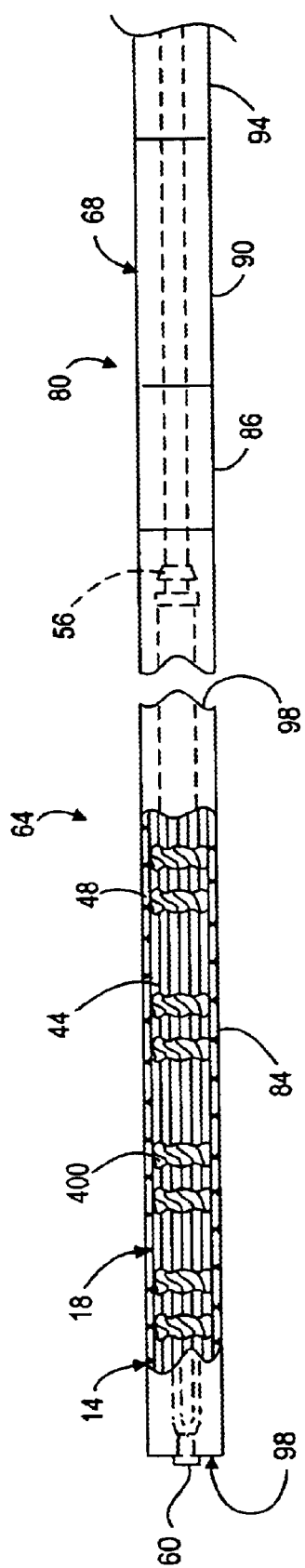
FIG. 6 is an enlarged side elevational view of a distal portion of the catheter illustrated in FIG. 1, with a portion of the catheter body removed to show the probe assembly in a collapsed condition.

The catheter 10 can be functionally divided into four regions: the operative distal probe assembly region 64, a deflectable catheter region 68, a main catheter region 72, and a proximal catheter handle region 76. A handle assembly 77 including a handle 78 is attached to the proximal catheter handle region 76 of the catheter 10. With reference to FIG. 6, the catheter 10 also includes a catheter body 80 that may include first and second tubular elements 84 and 86, which form, in conjunction, the structure of the distal probe assembly region 64; a third tubular element 90, which forms the structure of the deflectable catheter region 68; and a fourth tubular element 94, which forms the structure of the main catheter region 72. It should be noted, however, that the catheter body 80 may include any number of tubular elements required to provide the desired functionality to the catheter. The addition of metal in the form of a braided mesh layer sandwiched in between layers of the pliastic tubing may be used, greatly increasing the rotational stiffness of the catheter. This may be beneficial to practice one or more lesion creation techniques described in more detail below.

With reference to FIG. 2, the operative distal probe assembly region 64 includes the probe assembly 14. The catheter 10 may also include a sheath 98 that, when moved distally over the basket 18, collapses the basket 18 (FIG. 6). In a preferred embodiment, the microporous body 22 is collapsed (by the removal of the inflation medium 30 therefrom) before the basket 18 is collapsed; however, in an alternative embodiment, collapsing the basket 18 may cause fluid to be removed from the microporous body 22 and, thus, the microporous body 22 to collapse. Conversely, retracting the sheath 98 or moving the sheath 98 proximally away from the probe assembly 14 may deploy the basket 18. This removes the compression force causing the basket 18 to open to a prescribed three-dimensional shape moving the sheath 98 distally in the direction indicated by arrow 106 causes the sheath 98 to apply a compressive force, thus, collapsing the basket 18. Moving the sheath 98 proximally in the direction indicated by the arrow 110 removes the compressive force of the sheath 98, thus, allowing the basket 18 to expand.

Figure 1:
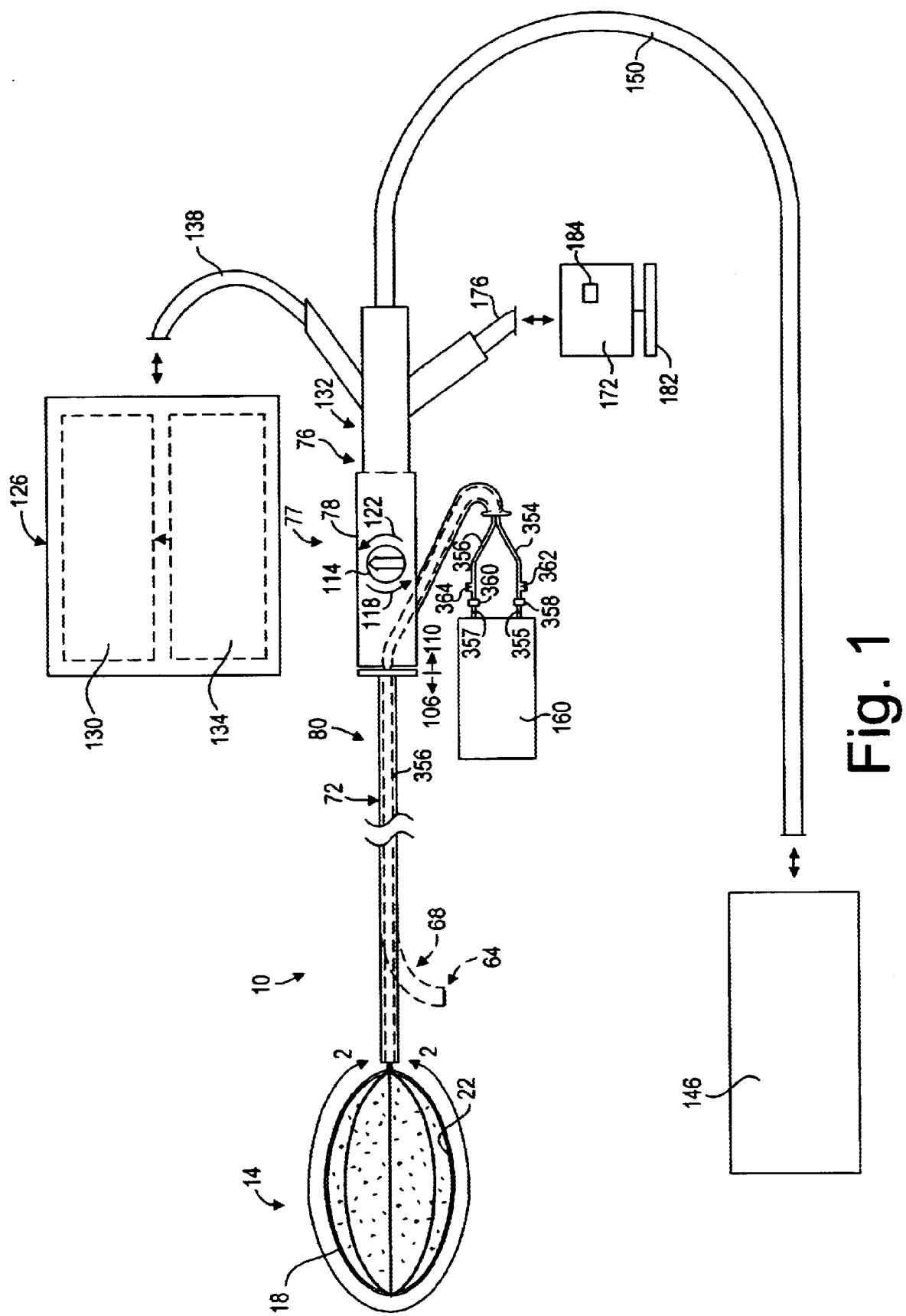
FIG. 1 is a schematic illustration of a RF mapping and ablation catheter system including a probe assembly constructed in accordance with a first aspect of the invention.

With reference to FIGS. 1, 2 and 6, the deflectable catheter region 68 is the steerable portion of the catheter 10, which allows the probe assembly 14 to be accurately placed adjacent the targeted tissue region. A steering wire (not shown) may be slidably disposed within the catheter body 80 and may include a distal end attached between the second tubular element 86 and the third tubular element 90 and a proximal end suitably mounted within the handle 78. The handle assembly 77 may include a steering member such as a rotating steering knob 114 that is rotatably mounted to the handle 78. Rotational movement of the steering knob 114 counter clockwise relative to the handle 78, in the direction indicated by the arrow 118, may cause a steering wire to move proximally relative to the catheter body 80 which, in turn, tensions the steering wire, thus pulling and bending the catheter deflectable region 68 into an arc (shown by broken lines in FIG. 1). On the contrary, rotational movement of the steering knob 114 clockwise relative to the handle 78, in the direction indicated by the arrow 122, may cause the steering wire to move distally relative to the catheter body 80 which, in turn, relaxes the steering wire, thus allowing the resiliency of the third tubular element 90 to place the catheter deflectable region 68 of the catheter back into a rectilinear configuration. To assist in the deflection of the catheter, the deflectable catheter region 68 is preferably made of a lower durometer plastic than the main catheter region 72.

The catheter 10 may be coupled to a RF generator 126 such as that described in Jackson et al., U.S. Pat. No. 5,383,874, the specification of which is fully and expressly incorporated herein by reference. The RF generator 126 provides the catheter 10 with a source of RF ablation energy. The RF generator 126 includes a RF source 130 for generating the RF energy and a controller 134 that controls the amplitude of, and time during, which the RF source 130 outputs RF energy. The RF generator 126 is electrically coupled to the catheter 10 via a cable 138. One or more signal wires 140 are routed through an ablation wire tubular member 142 (FIG. 2, 4) in the catheter body 80 and couple the ring electrode 40 to the cable 138. Operation of the RF generator 126 provides RF energy to the ring electrode 40, which in turn is ionically transferred through the inflation medium 30, and out through the pores of the microporous body 22, into the targeted tissue region. Thus, when operated, the RF generator 126 allows the physician to ablate body tissue such as pulmonary vein tissue in a controlled manner, resulting in a tissue lesion with the desired characteristics.

A mapping signal processor 146 may also be coupled to the catheter 10, allowing a physician to map the electrical activity in the target tissue site before, during and/or subsequent to the ablation process. The mapping processor 146 may be part of the controller 134. The mapping processor 146 is in electrical communication with the mapping electrodes 48 via a mapping cable 150 and the signal wires 52. The signal wires 52 are preferably routed, through a mapping wire tubular member 156 (FIG. 2, 4) in the catheter body 80.

An inflation medium reservoir and pump 160 may be coupled to the catheter 10 for supplying the microporous body 22 with the inflation medium 30. The reservoir and pump 160 may supply ionic fluid at room temperature or may include a chiller for supplying cool ionic fluid. A constant flow of ionic cooling fluid such as a 10% saline solution may be circulated through the microporous body 22 to cool the microporous body 22 and supply the ionic fluid necessary to allow ionic transfer through the body for ablation. An inlet lumen 354 and an outlet lumen 356 are adapted to communicate at proximal ends, inlet port 355 and outlet port 357, with the reservoir and pump 160 and at distal ends with the mouth or interior of the microporous body 22. Preferably, the fluid lumens 354, 356 have the same length and internal diameters, resulting in a microporous body pressure that is approximately half of that at the inlet port 355. The pressures at the inlet port 355 and outlet port 357 may be measured with respective inlet and outlet pressure sensors, 358, 360. Thus, the microporous body pressure may be estimated/controlled using the pressure measured at the inlet sensor 358.

The fluid is preferably circulated at a rate and pressure that maintains the fluid pressure in the microporous body 22 at a predetermined pressure. Alternatively, the microporous body pressure may be controlled by injecting the fluid into the inlet port 355 at a known, controlled rate.

The pump 160 may impart the pressure necessary to circulate the fluid through the microporous body 22 and the fluid may passively flow out of the outlet port 357. Alternatively, the pump 160 may apply a vacuum pressure to the outlet port 357 to increase the allowable flow rate through the microporous body 22.

An inlet control valve 362, e.g., pop-off valve, and/or outlet control valve 364 at the inlet 355 and/or outlet 357 may be used to prevent the microporous body 22 from being inflated above the body, burst pressure or a lower predefined pressure to prevent over-inflation or bursting, ensuring patient safety. A control valve set to a low pressure value may also be used to ensure that the body 22 remains inflated even when flow to the body 22 is stopped, if the pressure value exceeds that required to maintain body inflation.

A continuous flow of ionic fluid maintains the microporous body 22 and ablation site at a cooler temperature, allowing for more power delivery to the target tissue to make deeper lesions. The continuous flow also enables the use of a smaller RF electrode within the microporous body 22 because heat generated near the electrode can be convected away from that electrode. Finally, the continuous flow reduces the possibility that non-targeted adjacent tissue will be damaged, thereby increasing patient safety.

An auxiliary member 172 may be coupled to the catheter 10 via an external connector 176 and further coupled to the probe assembly 14 via an internal connector or carrier 180 (FIG. 4) in the catheter body 80. The one or more temperature sensors 50 on one or more of the splines 44 of the basket 18 may be connected to one or more temperature sensor wires guided through the internal connector or carrier 180 of the catheter body 80. The auxiliary member 172 may be a controller that is coupled to the one or more temperature sensor wires via the external connector 176. If the auxiliary member 172 is a controller, it is preferably the same as the controller 134 of the RF generator 126.

Temperatures sensed by the temperature sensors 50 are processed by the controller 172. Based upon temperature input, the controller 172 adjusts the time and power level of radio frequency energy transmissions by the RF generator 126, and consequently the ring electrode 40, to achieve the desired lesion patterns and other ablation objectives and to avoid undesired tissue necrosis caused by overheating.

Temperature sensing and controlling using the one or more temperature sensors 50 of the splines 44 will now be described in more detail. The controller 172 may include an input 182 for receiving from the physician a desired therapeutic result in terms of (i) the extent to which the desired lesion should extend beneath the tissue-electrode interface to a boundary depth between viable and nonviable tissue and/or (ii) a maximum tissue temperature developed within the lesion between the tissue-electrode interface and the boundary depth. The controller 172 may also include a processing element 184 that retains a function that correlates an observed relationship among lesion boundary depth, ablation power level, ablation time, actual sub-surface tissue temperature, and electrode temperature. The processing element 184 compares the desired therapeutic result to the function and selects an operating condition based upon the comparison to achieve the desired therapeutic result without exceeding a prescribed actuator predicted sub-surface tissue temperature.

The operating condition selected by the processing element 184 can control various aspects of the ablation procedure such as controlling the ablation power level, limiting the ablation time to a selected targeted ablation time, limiting the ablation power level subject to a prescribed maximum ablation power level, and/or the orientation of the microporous region 32 of the body 22, including prescribing a desired percentage contact between the region 32 and tissue.

If the ablating electrode(s) is the microporous body 22 or conventional metal electrode(s) where an expandable body is used to restrict blood flow around the electrode(s), the processing element 184 may rely upon the temperature sensors 50 to sense actual maximum tissue temperature because the body 22 restricts blood flow to the ablation site, minimizing convective cooling of the tissue-electrode interface by the surrounding blood flow. As a result, the region of maximum temperature is located at or close to the interface between the tissue and the microporous body 22. The temperature conditions sensed by the temperature sensors 50 closely reflect actual maximum tissue temperature.

If the ablating electrode(s) is a conventional metal electrode(s) and blood is free to flow over the electrode(s), the processing element 302 may predict maximum tissue temperature based upon the temperature sensed by the temperature sensors 50 at the tissue-electrode interface. When using a conventional metal electrode(s) to ablate tissue, the tissue-electrode interface is convectively cooled by surrounding blood flow. Due to these convective cooling effects, the region of maximum tissue temperature is located deeper in the tissue. As a result, the temperature conditions sensed by the temperature sensors 50 associated with metal electrode elements do not directly reflect actual maximum tissue temperature. In this situation, maximum tissue temperature conditions must be inferred or predicted by the processor 184 from actual sensed temperatures.

In a preferred embodiment, the one or more temperature sensors 50 are used to sense instantaneous localized temperatures (T1) of the thermal mass corresponding to the region 32. The temperature T1 at any given time is a function of the power supplied to the electrode 40 by the generator 126.

The characteristic of a lesion can be expressed in terms of the depth below the tissue surface of the 50 degree C. isothermal region, which will be called D.sub.50C. The depth D.sub.50C is a function of the physical characteristics of the microporous region 32 (that is, its electrical and thermal conductivities, resistivities, and size); the percentage of contact between the tissue and the microporous region 32; the localized temperature T1 of the thermal mass of the region 32; the magnitude of RF power (P) transmitted by the interior electrode 40, and the time (t) the tissue is exposed to the RF power.

For a desired lesion depth D.sub.50C, additional considerations of safety constrain the selection of an optimal operating condition among the operating conditions listed above. The principal safety constraints are the maximum tissue temperature TMAX and maximum power level PMAX.

The maximum temperature condition TMAX lies within a range of temperatures that are high enough to provide deep and wide lesions (typically between about 50 degree C. and 60 degree C.), but are safely below about 65 degree C., the temperature at which pulmonary stenosis is known to occur. It is recognized that TMAX will occur somewhere between the electrode-tissue interface and D.sub.50C. As discussed above, if the ablating electrode is the micropqrous body 22 or a conventional electrode(s) and an expandable body is used to restrict blood flow at the ablation site, TMAX will be closer to the interface because of the lack of convective cooling by the blood flow. If the ablating electrode is a conventional metal electrode(s) and nothing restricts blood flow to the ablation site, TMAX will be deeper in the tissue because of the convective cooling of the electrode(s) by the blood flow.

The maximum power level PMAX takes into account the physical characteristics of the interior electrode 40 and the power generation capacity of the RF generator 126. The D.sub.50C function for a given porous region 32 can be expressed in terms of a matrix listing all or some of the foregoing values and their relationship derived from empirical data and/or computer modeling. The processing element 184 includes in memory this matrix of operating conditions defining the D.sub.50C temperature boundary function for multiple arrays of operating conditions.

The physician also uses the input 182 to identify the characteristics of the structure 22, using a prescribed identification code; set a desired maximum RF power level PMAX; a desired time t; and a desired maximum tissue temperature TMAX.

Based upon these inputs, the processing element 184 compares the desired therapeutic result to the function defined in the matrix, and selects an operating condition to achieve the desired therapeutic result without exceeding the prescribed TMAX by controlling the function variables.

Using the microporous body 22, typical ablation conditions are to control to sensed temperatures of 65 degree C and apply RF power for one minute.

With reference back to FIG. 4, the internal carrier 180 (or an internal carrier similar to the internal carrier 18) may be used as a transport lumen for drug delivery via the body 22 (if the pores were large enough and/or the drug molecules small enough) or other means. The internal carrier 180 may terminate in the handle assembly 77, where a physician may inject the medicine into the internal carrier 180 or the medicine may be supplied by the auxiliary; member 172 . The medicine may travel through the internal carrier 180 to the body 22. Additional or fewer auxiliary components may be used depending on the application.

C. Method of Use

With reference to FIGS. 1–6, a method of using the catheter 10 and probe assembly 14 will now be described. Before the catheter 10 can be introduced into a patient's body, the probe assembly 14 must be in a collapsed condition (FIG. 6). If the catheter 10 is not already in this condition, the probe assembly 14 can be collapsed by moving the sheath 98 forward, towards the distal end of the catheter 10 (in the direction indicated by the arrow 106).

Placement of the catheter 10 within the vasculature of the patient is typically facilitated with the aid of an introducer guide sheath or guide wire, which was previously inserted into the patient's vasculature, e.g., femoral vein. The introducer guide sheath is introduced into the left atrium of the heart using a conventional retrograde approach, i.e., through the respective aortic and mitral valves of the heart. One or more well-known visualization devices and techniques, e.g., ultrasound, fluoroscopy, etc., may be used to assist in navigating and directing the catheter 10 to and from the targeted region. Alternatively, the introducer guide sheath may be introduced into the left atrium using a conventional transeptal approach, i.e., through the vena cava and atrial septum of the heart. A detailed description of methods for introducing a catheter into the left atrium via a transeptal approach is disclosed in U.S. Pat. No. 5,575,810, issued to Swanson et al., which is fully and expressly incorporated herein by reference.

In either method (conventional retrograde approach or transeptal approach), the catheter 10 is introduced through the introducer guide sheath until the probe assembly 14 resides within the left atrium. Once inside the left atrium, the physician may deliver the probe assembly 14 into a desired pulmonary vein through rotational movement of the steering knob 114 on the catheter handle 78. The physician situates the probe assembly 14 within a selected tissue region in the interior of the pulmonary vein, adjacent to the opening into the left atrium. The basket 18 is deployed by moving the sheath 98 proximally in the direction indicated by the arrow 110, causing the sheath 98 to slide away from the basket 18 and removing the compression force thereon. The basket 18 then expands, allowing one or more of the mapping electrodes 48 to contact the pulmonary vein tissue.

The mapping electrodes 48 are used to sense electrical activity in the pulmonary vein tissue, and may be used to pace pulmonary vein tissue as well. Mapping data received and interpreted by the mapping signal processor 146 is displayed for use by the physician to locate aberrant pulmonary vein tissue. The probe assembly 14 may be moved one or more times, which may require collapsing and deploying the probe assembly 14 one or more times, in an effort to locate aberrant pulmonary vein tissue.

When the physician has determined that the aberrant pulmonary vein tissue has been located (basket 18 is deployed), the physician may then expand the microporous body 22 by filling the microporous body 22 with the inflation medium 30 to contact the targeted pulmonary veinitissue. The pump 160 may be activated to introduce the ionic fluid through the inlet lumen 354 and into the microporous body 22 at a constant pressure, inflating the body 22. The ionic fluid circulated may be cool or at room temperature. The ionic fluid exits the microporous body 22 and flows through the outlet lumen 356 to the outlet 357. The fluid may passively drip or flow out of the outlet lumen 356, or may be drawn out of the outlet lumen 356 with vacuum pressure from the pump 160. Inflating or maintaining the microporous body 22 at less than full pressure is desirable because a non-turgid microporous body 22 better conforms to the tissue surface.

Once the physician has determined that the microporous body 22 is effectively inflated and in contact with the pulmonary vein tissue, the physician may begin ablating the targeted tissue. RF energy is preferably supplied to the ring electrode 40, which is located within the microporous body 22 and surrounded by inflation medium 30. Through ionic transport, the electrical energy from the electrode 40 is transported through the inflation medium 30 and through the pores of the microporous body 22, to the exterior of the microporous body 22, into and through at least a portion of the pulmonary vein tissue so as to ablate the targeted pulmonary vein tissue, and to a return electrode.

If the electrodes 48 are also (or alternatively) used to ablate the pulmonary vein tissue and saline or a fluid having similar heat transfer characteristics is used to deploy the body 22, thermal transfer within the body may enable contiguous lesion formation between the electrodes 48 to be created more consistently.

Throughout this process the physician may monitor the temperatures of the tissue region using the temperature sensors 50 to more accurately ablate the target tissue.

Once ablation is completed, or in between ablation treatments, electrical activity in the pulmonary vein tissue may be mapped using the mapping electrodes 48 to confirm effective ablation treatment.

To collapse the probe assembly 14, the inflation medium 30 in microporous body 106 is removed, but no longer supplied, causing the microporous body 106 to deflate. The basket 18 is also collapsed by moving the sheath 98 forward, towards the distal end of the catheter 10 (in the direction indicated by the arrow 106). The catheter 10 is then removed from the patient's body or moved to a different location for additional diagnosis and/or treatment.

Thus, the probe assembly 14 and method described above are advantageous because they allow the physician to map and ablate the targeted pulmonary vein region with a single probe assembly positioning. Prior to the present invention, the physician would introduce the mapping electrode and map the aberrant region of the pulmonary vein, then remove that mapping electrode, and follow with the ablation electrode to ablate the aberrant region. Problems with the prior approach include the possibility of misdirecting or misplacing the ablating electrode and inadvertently ablating non-aberrant, i.e., healthy, pulmonary vein tissue, and the excessive time-consumption because the physician had to introduce and remove two catheters. This leads to more patient discomfort and room for physician error. Further, the apparatuses and methods of the present invention incorporate all the advantages of an expandable and collapsible microporous body with those of a mapping basket assembly.

Figure 7:
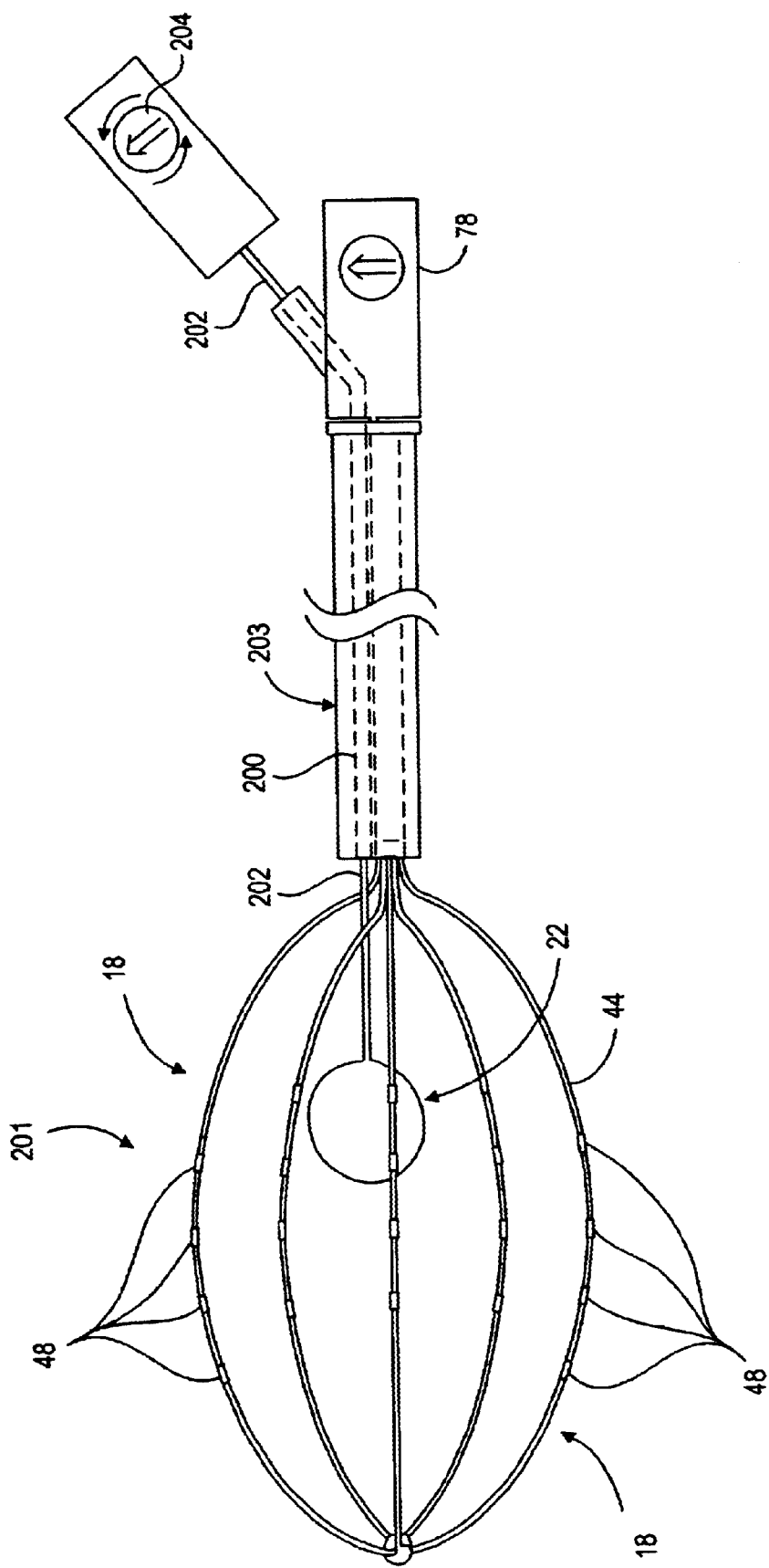
FIG. 7 is an enlarged side elevational view of an alternate embodiment of the probe assembly.

With reference to FIG. 7, in an alternative embodiment, a probe assembly 201 is comprised of elements from separate catheters, namely, a microporous body 22 from an ablation catheter 202 and a basket 18 from a main catheter 203. The basket 18 may include electrodes 48 that are adapted to map, pace, and/or ablate pulmonary vein tissue.

The ablation catheter 202 is slidably removable with respect to the main catheter 203 for positioning the microporous body 22 within or removing it from the basket 18. The catheter body 203 may include an additional lumen 200 through which the ablation catheter 202 may be slidably disposed.

Both the distal portions of the ablation catheter 202 and the main catheter 203 are preferably steerably controllable in a manner similar to that described above with respect to the catheter 10.

The microporous body 22 may range in size in the expanded state from the size of one of the electrodes 48 to just larger than the diameter of the basket 18. The active band 32 of the body 22 is preferably relatively large to better ensure lesion creation. In one embodiment, the body 22, when expanded, is large enough to create a circumferential lesion in the vein or around the ostium.

However, placement of lesion around the entire circumference is often not required to electrically isolate the pulmonary veins in atrial fibrillation patients. Therefore, in another exemplary embodiment, the expanded microporous body 22 is smaller than the pulmonary vein diameter or vein orifice to create one or more ablation sectors of the pulmonary vein, decreasing the probability of creating clinically significant pulmonary stenosis compared to a complete circumferential lesion. Additionally, a smaller microporous body 22 enables blood flow in pulmonary veins to continue during ablation.

A method of using the probe assembly 201 is similar to that described above with respect to the probe assembly 14, except the main catheter 203 and ablation catheter 202 may be introduced separately to the targeted site. The ablation catheter 202 may be introduced into the lumen 200 of the main catheter 203 via the handle 78 and snaked through the lumen 200 until the collapsed microporous body 22 is located within the basket 18. The physician may then inflate the microporous body 22 and steer the body 22 so that it contacts the targeted pulmonary vein tissue. As discussed above, inflation of the microporous body 22 at a pressure corresponding to a less than fully expanded state may be desirable because a non-turgid body 22 better conforms to the tissue surface than a turgid body 22. The microporous body 22 may be maintained in an expanded state by continuously circulating a fluid medium through the body 22 as described above or by inflating the body 22 with the medium and preventing the medium from exiting the catheter.

For sectional ablation (i.e., non-circumferential ablation), a relative small, expanded microporous body 22 such as that illustrated in FIG. 7 may be used to ablate one or more targeted areas. Additionally or alternatively, the electrodes 48 may be used to ablate one or more targeted areas. If the electrodes 48 are used to ablate tissue, the body 22 may be used to restrict blood flow from the ablation area.

For circumferential ablation, a larger, expanded microporous body 22 such as that illustrated in FIG. 2 and 5 may be used. A larger, expanded microporous body 22 restricts blood flow to the ablation site, increasing the efficiency of the ablation since RF currents flow substantially into the tissue only, and not into the blood. Restricting blood flow also reduces the possibility of coagulated blood embolus and renders the relationship between ablation parameters (power, time and temperature) and lesion characteristics more predictable since fewer uncontrolled variables exists (mostly attributable to convective losses and to energy delivery to tissue). Further, if the electrodes 48 are also used to ablate the pulmonary vein tissue and saline or a fluid having similar heat transfer characteristics is used to deploy the body 22, thermal transfer within the body 22 may enable contiguous lesion formation between the electrodes 48 to be created more consistently. Also, the microporous body 22 may create a lossy electrical connection between the electrodes 48 that may enable contiguous lesion formation between the electrodes 48 to be created more consistently.

Figure 8:
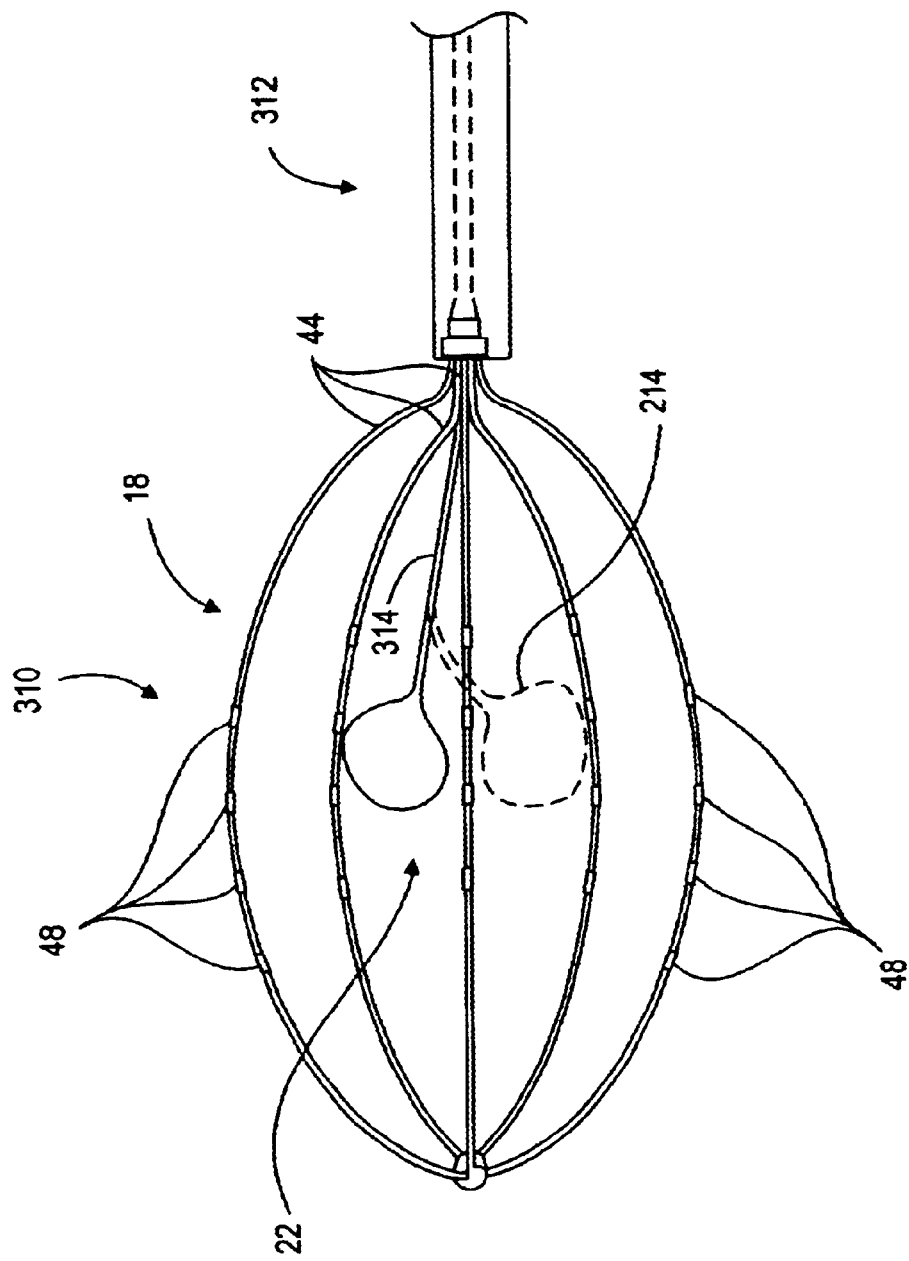
FIG. 8 is an enlarged side elevational view of a further embodiment of the probe assembly.
Figure 9:
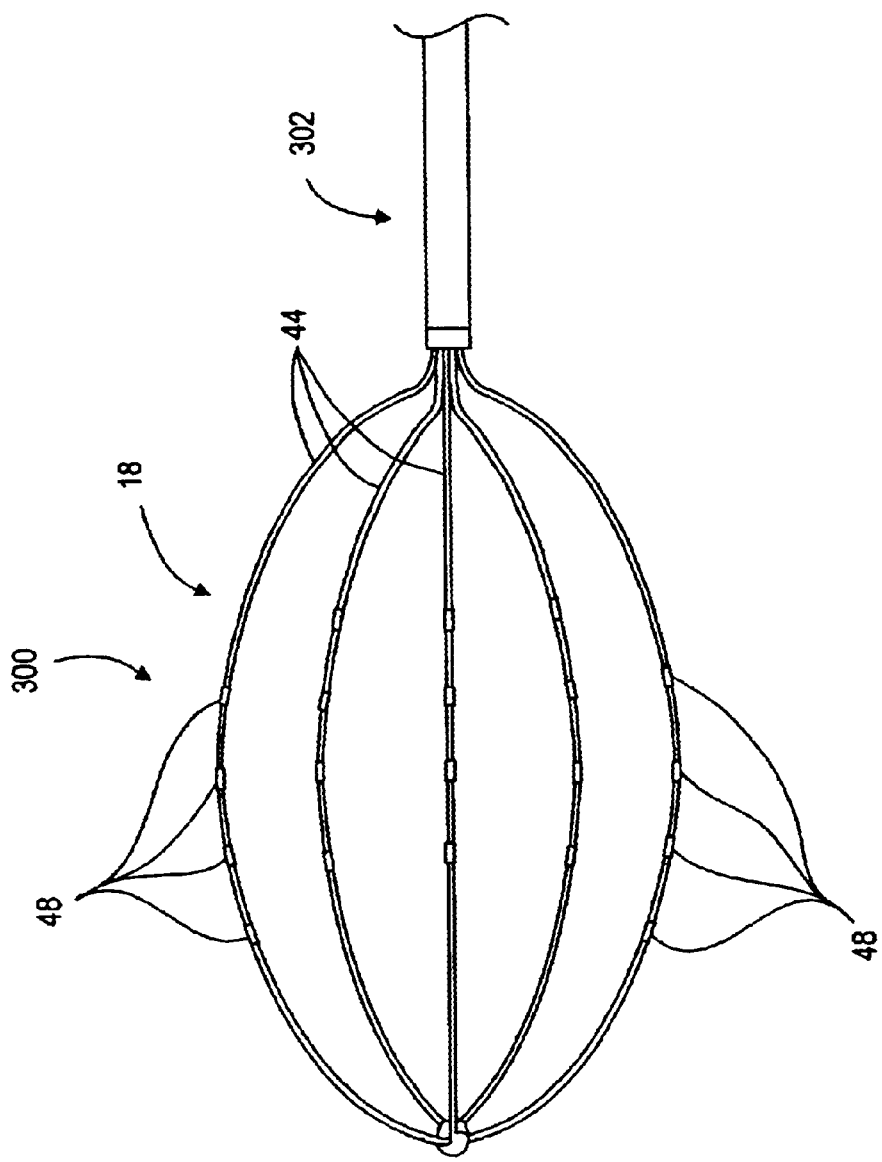
FIG. 9 is an enlarged side elevational view of a probe assembly constructed in accordance with a second aspect of the invention.

With reference to FIG. 8, in a further embodiment, a probe assembly 310 includes a basket 18 located at a distal end of a catheter 312 and a microporous body 22 integrated with the basket 18. The microporous body 22 may be located at the distal end of a steerable member 314 that is steerable in a manner similar to that described above with respect to catheter 10. The probe assembly 310 is similar to the probe assembly 201 described above with respect to FIG. 7, except the microporous body 22 and steerable member 314 are not removable from the catheter 202. The catheter 312 is also steerable in a manner similar to that described with respect to catheter 10. The microporous body 22, when expanded, can range in size from the size of a single spline electrode 48 to a large body that will be large enough to fill the entire inner cavity of the basket 18.

The method of using the probe assembly 310 is similar to that described above with respect to probe assembly 201, except a separate ablation catheter is not snaked through a main catheter or removed therefrom because the microporous body 22 and steerable member 314 are integrated with the basket 18.

2. Probe Assembly with a Basket Assembly for Mapping and Ablating Pulmonary Vein Tissue With reference to FIGS. 9 and 10A–10D, a second aspect of a probe assembly 300 of a mapping and ablation catheter 302 will now be described. Unlike the prior embodiments, the probe assembly 300 does not include a microporous body. Instead, the probe assembly 300 includes a basket 18 with a plurality of multi-functional electrodes 48 adapted to map and ablate body tissue. The catheter 302 is preferably steerable in a manner similar to that described above with respect to catheter 10.

The number of electrodes 48 that each spline 44 carries, the spacing between the electrodes 48, and the length of the electrodes 48 may vary according to the particular objectives of the ablating procedure. These structural features influence the characteristics of the lesion patterns formed.

Segmented electrodes 48 may be well suited for creating continuous, elongated lesion patterns provided that the electrodes 48 are adjacently spaced close enough together to create additive heating effects when ablating energy is transmitted simultaneously to the adjacent electrodes 48. The additive heating effects between close, adjacent electrodes 48 intensify the desired therapeutic heating of tissue contacted by the electrodes 48. The additive effects heat the tissue at and between the adjacent electrode 48 to higher temperatures than the electrode 48 would otherwise heat the tissue, if conditioned to individually emit energy to the tissue. The additive heating effects occur when the electrodes 48 are operated simultaneously in a bipolar mode between electrodes. Furthermore, the additive heating effects also arise when the electrodes are operated simultaneously in a unipolar mode, transmitting energy to an indifferent electrode.

Conversely, when the electrodes 48 are spaced sufficiently far apart from each other, the electrodes 48 create elongated lesion segments.

The length of each electrode 48 may also be varied. If the electrode 48 is too long, the ability of the splines 44 to conform to the anatomy of the pulmonary vein may be compromised. Also, long electrodes may be subject to "hot spots" during ablation caused by differences in current density along the electrode. Another approach is to use multiple short electrodes 48 on each spline 44 to cover a large effective ablating length and avoid hot spots. An electrode approximately 3 mm in length or less makes an adequate lesion without hot spots, although other lengths may also work.

Ablating energy can be selectively applied individually to just one or a selected group of electrodes, when desired, to further vary the size and characteristics of the lesion pattern.

A basket 18 including eight splines 44 should be adequate for ablating in pulmonary veins of 10 to 15 mm in diameter; however, the basket 18 may have a greater or lesser number of splines 44, depending on the size of the target anatomy. A small vein may require fewer splines 44 than a larger vein to form a continuous circular lesion around the circumference of the vein.

The method of using the probe assembly 300 is similar to that described above for the probe assembly 14, except once the basket 18 is at the appropriate location, the physician may begin ablation using the same electrodes 48 that were used to map electrical activity in the pulmonary vein tissue. Should the physician decide that only one section or certain sections of the vein 304 needs ablation, the physician may activate RF energy to select electrodes 44 corresponding to the section or sections of the vein 304.

Figure 10A:
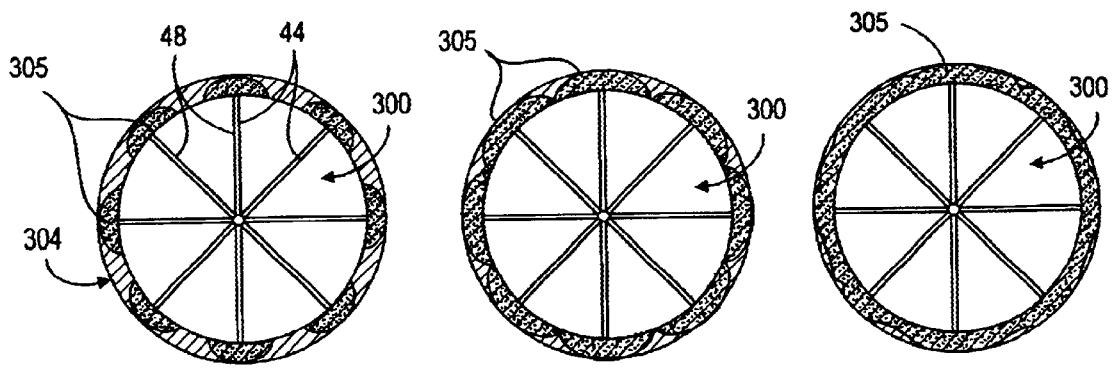
FIGS. 10A–10C are cross sectional views of the probe assembly illustrated in FIG. 9, and depict alternative embodiments of lesion creating techniques.

With reference additionally to FIG. 10A, if the physician decides that the entire circumference of the pulmonary vein 304 needs treatment and the vein 304 is relatively small relative to the number of splines 44 of the probe assembly 300, the physician may simply activate RF energy once to all the electrodes 48 or to certain circumferential electrodes 44.

Figure 10B:
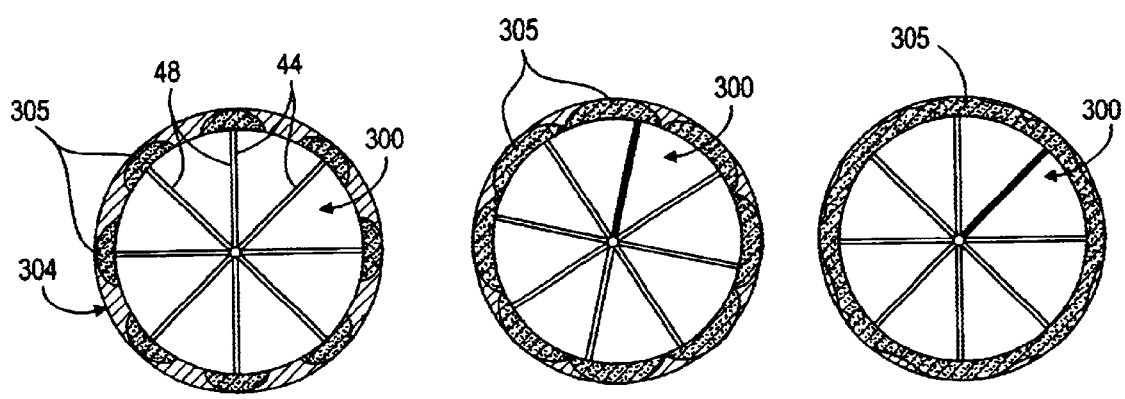

With reference to FIG. 10B, in an alternate lesion-making technique, where a single ablation step such as that described above with respect to FIG. 10A proves insufficient to form an unbroken lesion line in larger veins 304, the catheter 302 may be rotated slightly, and a second ablation may be performed. One or more successive rotations and ablations with the probe assembly 300 may be necessary in order to make a contiguous lesion 305.

Figure 10C:
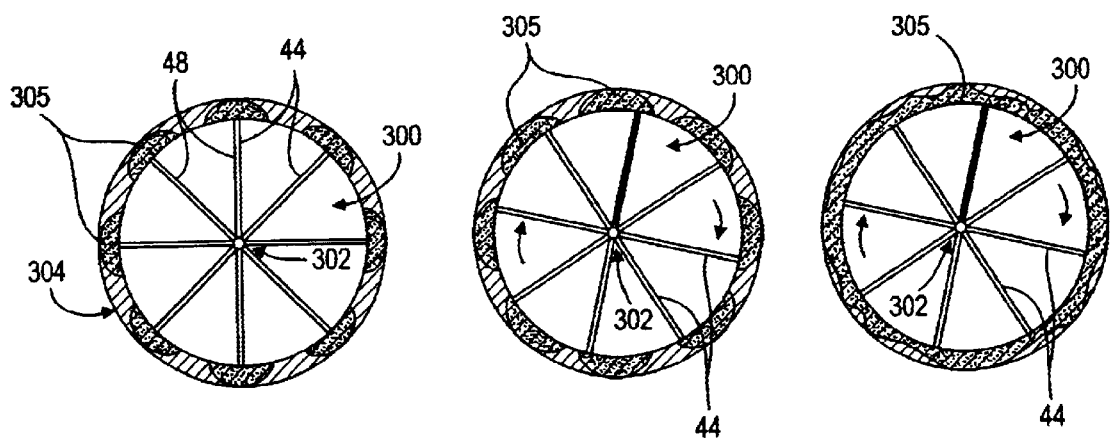

With reference to FIG. 10C, in a further lesion-making technique, the catheter 302 may be rotated while simultaneously ablating the pulmonary vein 304. The handle 76 (FIG. 1) of the catheter 302 may be rotated slowly until the lesion 305 made by one spline 44 begins to overlap the lesion 305 started by an adjacent spline 44.

After a first round of ablation, the physician may then take further electrode 44 readings, retract the basket 18, and reposition the catheter 302 for further ablation procedures or, if done, remove the catheter 302 from the patient's vasculature.

Figure 11:
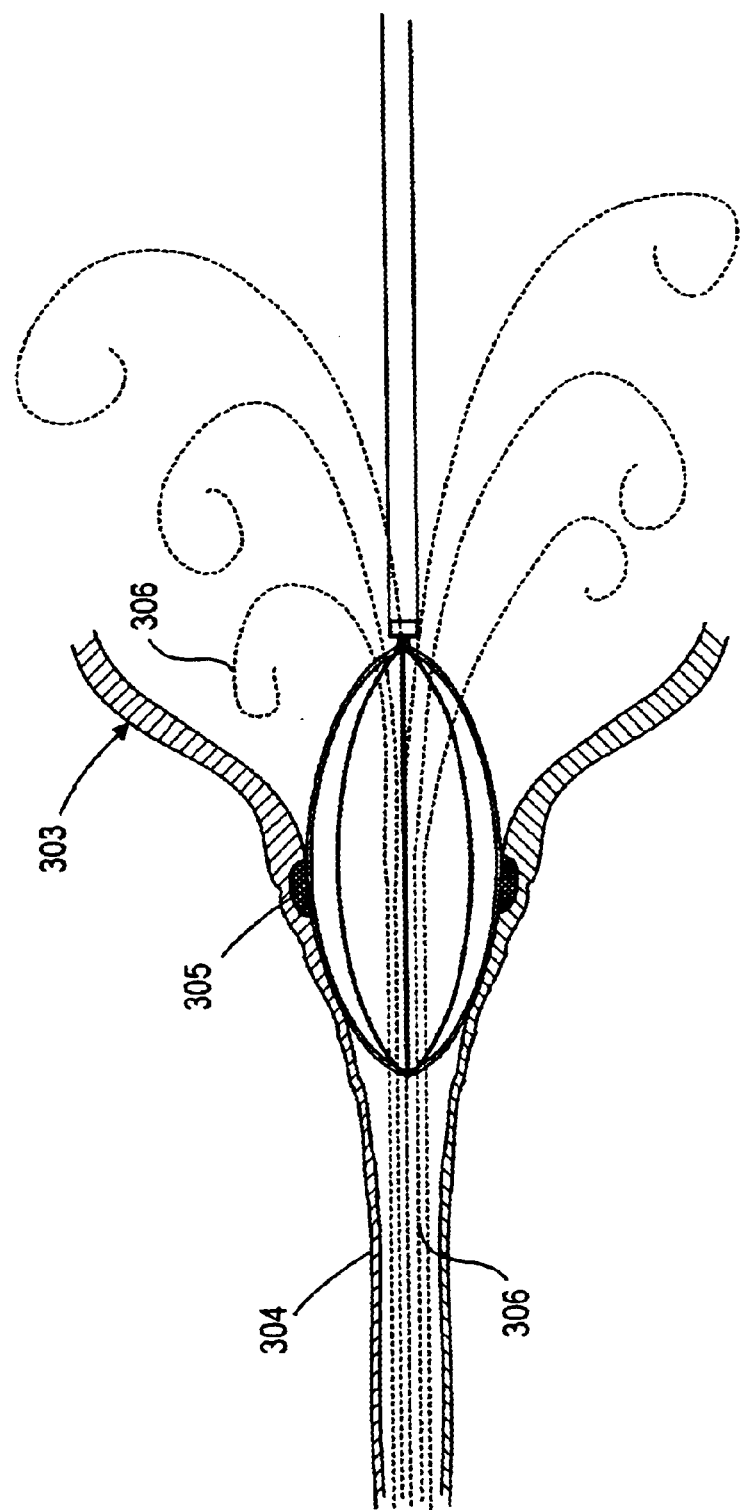
FIG. 11 is an enlarged side elevational view of the probe assembly illustrated in FIG. 9 placed at the ostium of a pulmonary vein.

With reference to FIG. 11, an advantage to this aspect of the invention is that the probe assembly 300 does not include a structure likely to block significant blood flow 306 or otherwise occlude the vein 304. Sufficient blockage can cause hemodynamic compromise in some patients. In addition, blood flow 306 has a beneficial cooling effect that allows the probe assembly 300 to create deeper lesions at lower temperatures and inhibit damaging non-target adjacent tissue. Finally, this embodiment contains separate electrodes 48 that can create lesions at selected sections of the vein 304 or around the entire circumference by one of the lesion-creating techniques described above.

Figure 12:
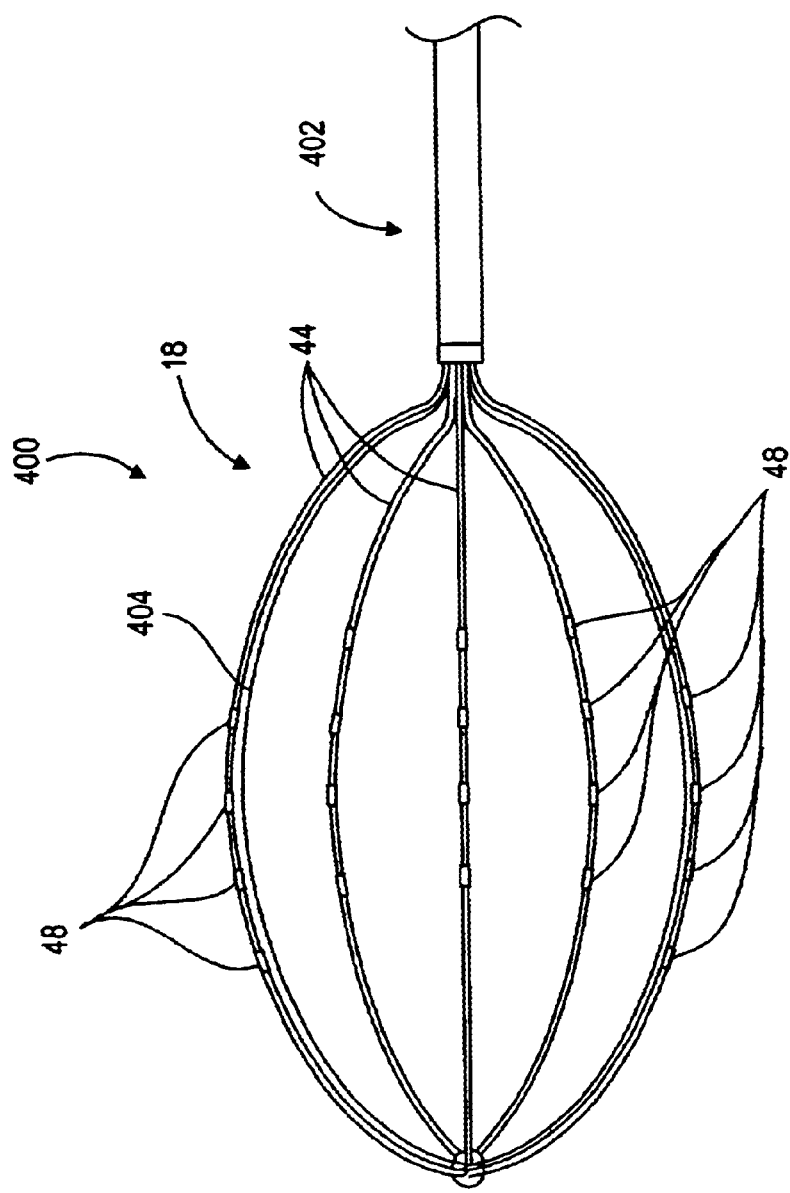
FIG. 12 is an enlarged side elevational view of a probe assembly constructed in accordance with a third aspect of the invention.

3. Probe Assembly with an Expandable Body used with a Basket Assembly for Mapping and Ablating Pulmonary Vein Tissue With reference to FIG. 12, a probe assembly 400 constructed in accordance with a further aspect of the invention will now be described. The probe assembly 400 is located at a distal end of a catheter 402 that is preferably steerably controlled in a manner similar to that described above with respect to catheter 10. The probe assembly 400 is similar to probe assembly 300 described above with respect to FIG. 9, i.e., includes multi-functional electrodes 48 that may map, pace and/or ablate, except the probe assembly 400 further includes a non-porous, non-electrically conducting expandable balloon 404. The non-porous, non-electrically conducting balloon 404 includes the following two primary functions: (1) to assist in maintaining the position of the basket structure 18 by placing some force against the vein walls, and (2) to restrict blood flow to the ablation area.

A method of using the probe assembly 400 will now be described. A physician may guide the catheter 402 to the appropriate location and deploy the basket 18. Electrical activity in the pulmonary vein may be mapped using the multi-function electrodes 48 on the splines 44. The physician may interpret the resulting electrical activity data, and determine the proper position of the probe assembly 400 for ablation.

Once satisfied that the position is accurate, the physician may inflate the non-electrically conducting body 404 with a fluid such as saline or $CO_2$ and perform ablation of the targeted tissue with the electrodes 48. As described above with respect to body 22, the fluid may be constantly circulated though the body 404.

The expanded body 404 restricts blood flow to the ablation site, increasing the efficiency of the ablation since RF currents flow substantially into the tissue only, and not into the blood. Restricting blood flow also reduces the possibility of coagulated blood embolus and renders the relationship between ablation parameters (power, time and temperature) and lesion characteristics more predictable since fewer uncontrolled variables exist (mostly attributable to convective losses and to energy delivery to tissue). If saline or a fluid having similar heat transfer characteristics is used to deploy the body 404, thermal transfer within the body 404 may enable contiguous lesion formation between the electrodes 48 to be created more consistently.

While preferred methods and embodiments have been shown and described, it will be apparent to one of ordinary skill in the art that numerous alterations may be made without departing from the spirit or scope of the invention. Therefore, the invention is not to be limited except in accordance with the following claims.

We claim:

1. A probe assembly for mapping and ablating pulmonary vein tissue, comprising an expandable and collapsible basket assembly including multiple splines, one or more of said splines carrying one or more electrodes adapted to sense electrical activity in said pulmonary vein tissue, said basket assembly defining an interior; and an expandable and collapsible body disposed in the interior of said basket assembly and defining an interior adapted to receive a fluid medium for expanding said expandable and collapsible body, said expandable and collapsible body expandable to substantially occupy said interior of said expandable and collapsible basket;

wherein said expandable and collapsible body is a microporous expandable and collapsible body defining an interior adapted to receive a medium containing ions, an internal electrode disposed within said interior of said body and adapted to transmit electrical energy to said medium containing ions, said body including at least one microporous region having a plurality of micropores therein sized to pass ions contained in the medium without substantial medium perfusion therethrough, to thereby enable ionic transport of electrical energy from the internal electrode, through the ion-containing medium to an exterior of the body to ablate pulmonary vein tissue.

2. The assembly of claim 1, wherein the body is made of a poly(vinylidene fluoride) and poly(vinylpyrrolidone) combination.

3. The assembly of claim 1, wherein said body includes at least one customized microporous region with a predetermined geometry to more efficiently produce a desired lesion characteristics.

4. The assembly of claim 1, wherein said body is adapted to extend between and beyond the circumferential region defined by said basket assembly when said basket assembly and said body are in an expanded state.

5. The assembly of claim 1, wherein said body when expanded is sized to create a circumferential lesion in the pulmonary vein or around the ostium.

6. The assembly of claim 1, wherein said body when expanded is smaller in size than the vein orifice so as to allow blood flow thereby, and said body is adapted to sectionally ablate the pulmonary vein or vein ostium.

7. The assembly of claim 1, wherein said microporous body is integrated with said basket assembly.

8. The assembly of claim 1, wherein said microporous body is removable from said basket assembly.

9. The assembly of claim 1, wherein said microporous body and basket assembly are separately steerable.

10. The assembly of claim 1, wherein said one or more electrodes are adapted to also ablate pulmonary vein tissue.

11. The assembly of claim 10, wherein said microporous body when expanded is adapted to exclude blood from said electrodes.

12. The assembly of claim 1, wherein said microporous body is adapted to be maintained in an expanded condition at a substantially constant pressure by a continuous flow of said medium therethrough, providing a cooling effect in said microporous body and pulmonary vein tissue.

13. The assembly of claim 12, further including an inlet lumen adapted to continuously deliver said medium to said microporous body and an outlet lumen adapted to continuously withdraw said medium from said microporous body.

14. A probe assembly for mapping and ablating pulmonary vein tissue, comprising an expandable and collapsible basket assembly including multiple splines, one or more of said splines carrying one or more electrodes adapted to sense electrical activity in said pulmonary vein tissue, said basket assembly defining an interior; and an expandable and collapsible body disposed in the interior of said basket assembly and defining an interior adapted to receive a fluid medium for expanding said expandable and collapsible body, said expandable and collapsible body expandable to substantially occupy said interior of said expandable and collapsible basket;

wherein said non-porous expandable and collapsible body is a non-porous expandable and collapsible body, and is adapted to be maintained in an expanded condition at a substantially constant pressure by a continuous flow of said medium therethrough, providing a cooling effect in said non-porous expandable and collapsible body and pulmonary vein tissue.

15. The assembly of claim 14, further including an inlet lumen adapted to continuously deliver said medium to said non-porous expandable and collapsible body and an outlet lumen adapted to continuously withdraw said medium from said non-porous expandable and collapsible body.

16. The assembly of claim 1, wherein said expandable and collapsible body includes an interior adapted to receive a cryogenic medium to thereby enable cryogenic ablation of pulmonary vein tissue via said cryogenic medium and said body.

17. The assembly of claim 1, wherein said probe assembly includes a drug delivery mechanism adapted to deliver one or more drugs to pulmonary vein tissue or adjacent tissue.

* * * * *

UNITED STATES PATENT AND TRADEMARK OFFICE
CERTIFICATE OF CORRECTION

PATENT NO. : 6,640,120 B1
DATED : October 28, 2003
INVENTOR(S) : David K. Swanson et al.

It is certified that error appears in the above-identified patent and that said Letters Patent is hereby corrected as shown below:

Column 8,
Line 43, replace "shape moving" with -- shape. Moving --

Column 9,
Line 37, replace "routed, through" with -- routed through --

Column 10,
Line 8, replace "body, burst" with -- body's burst --
Line 60, replace "actuator" with -- actual or --

Column 11,
Line 59, replace "micropqrous" with -- microporous --

Column 12,
Line 31, replace "auxiliary;" with -- auxiliary --

Column 13,
Line 22, replace "veinitissue" with -- vein tissue --

Signed and Sealed this

Thirteenth Day of July, 2004

JON W. DUDAS
*Acting Director of the United States Patent and Trademark Office*